(12) United States Patent
Ariav et al.

(10) Patent No.: US 7,313,491 B2
(45) Date of Patent: Dec. 25, 2007

(54) METHOD AND APPARATUS FOR HIGH-PRECISION MEASUREMENT OF FREQUENCY

(75) Inventors: Arie Ariav, Doar-Na Hof Ashkelon (IL); Vladimir Ravitch, Ashkelon (IL)

(73) Assignee: Nexense Ltd., Yavne (IL)

( * ) Notice: Subject to any disclaimer, the term of this patent is extended or adjusted under 35 U.S.C. 154(b) by 38 days.

(21) Appl. No.: 11/329,104

(22) Filed: Jan. 11, 2006

(65) Prior Publication Data

US 2006/0155512 A1 Jul. 13, 2006

(30) Foreign Application Priority Data

Jan. 13, 2005 (IL) .................................. 166292

(51) Int. Cl.
*G01R 23/00* (2006.01)
*G01R 23/02* (2006.01)
(52) U.S. Cl. .................................... 702/75; 324/76.39
(58) Field of Classification Search ................. 702/75; 324/76.39; 714/811
See application file for complete search history.

(56) References Cited

U.S. PATENT DOCUMENTS 4,769,777 A * 9/1988 Bittle et al. .................. 708/251

6,194,937 B1 * 2/2001 Minami ....................... 327/270
2004/0059524 A1 * 3/2004 Watson et al. ................. 702/45

FOREIGN PATENT DOCUMENTS

JP 2004-228329 * 8/2004

* cited by examiner

*Primary Examiner*—Michael P. Nghiem
*Assistant Examiner*—Cindy D. Khuu

(57) ABSTRACT

A method and apparatus for measuring the frequency of a cyclically-repeating electrical signal by: passing the electrical signal through a network of sequentially-activated gates, in which the first gate detects the leading edge of each cycle of the electrical signal, and each of the remaining gates, when activated, applies a predetermine propagation delay to the detected leading edges; determining the gates which were activated at the beginning, and at the end, of a predetermined time window; determining the difference in the total propagation delays at the outputs of the activated gates; and utilizing the differences in the total propagation delays in determining the frequency of the electrical signal.

41 Claims, 2 Drawing Sheets

METHOD AND APPARATUS FOR HIGH-PRECISION MEASUREMENT OF FREQUENCY

RELATED APPLICATIONS

This application includes subject matter, and claims the priority date of Israel Patent Application No. 166292, filed on Jan. 13, 2005, the contents of which are incorporated herein by reference.

FIELD AND BACKGROUND OF THE INVENTION

The present invention relates to a high-precision measuring method and apparatus for measuring the frequency of a cyclically-repeating electrical signal. The invention is particularly useful in, and is therefore described below with respect to, the high-precision measuring method and apparatus described in prior U.S. Pat. No. 6,621,278 or U.S. Pat. No. 7,080,554, the contents of which patent and published application are expressly incorporated herein by reference.

As brought out in U.S. Pat. No. 6,621,278, and published U.S. Pat. No. 7,080,554 many measuring techniques are known for measuring or monitoring distance, displacement, temperature, pressure, force, and other parameters or conditions, but such known techniques generally increase in cost and complexity according to the precision desired, and also generally have an upper limit as to the precision practically attainable by the technique. For example, the measurement of distance of meters or kilometers with a precision of microns or fractions of a micron is extremely expensive, if attainable at all. The same limitations apply with respect to measuring temperature, force, and many other parameters or conditions.

U.S. Pat. No. 6,621,278 describes an extremely high-precision method and apparatus for measuring a predetermined parameter, or for monitoring a predetermined condition, having a known relation to or influence on the transit time of movement of an energy wave through a medium. The described method broadly involves transmitting a cyclically-repeating wave of the energy through a transmission channel in the medium from a transmitter to a receiver at the opposite ends of the transmission channel; continuously changing the frequency of the transmission according to changes in the monitored condition while maintaining the number of waves in a loop including the transmission channel as a whole integer; and utilizing the changes in frequency of the transmission to provide a measurement of the parameter or an indication of the monitored condition.

According to a preferred embodiment described in both of the above-cited patent and patent applications, the frequency of the transmission is continuously changed according to changes in the monitored condition by detecting a predetermined fiducial point in each cyclically-repeating energy wave received by the receiver, and changing the frequency of the transmitter in accordance with the detected fiducial point of each received energy wave such that the number of energy waves in the loop of the transmission channel is a whole integer. A second embodiment is described in the above-cited published patent application wherein the above operation is performed by a phase-locked loop circuit having an input from the receiver and an output controlling the transmitter. In both described embodiments, the changes in frequency of the wave transmission are measured to provide a measurement of the predetermined parameter, or an indication of the predetermined condition.

A conventional way of measuring frequency of a cyclically-repeating electrical signal is to count the number of cycles over a predetermined time period, and divide the counted number of cycles by the predetermined time period. However, where the electrical signal may vary in phase, such as in the above-described applications, such a measurement would produce an error which may vary up to the period of one cycle. For example, when measuring electrical signals in the order of one MHz, the error may be up to one microsecond, which corresponds to a frequency error of about 1000 Hz.

OBJECTS AND BRIEF SUMMARY OF THE PRESENT INVENTION

One object of the present invention is to provide a method and apparatus for measuring with high-precision the frequency of a cyclically-repeating electrical signal. Another object of the present invention is to provide a method and apparatus for measuring a predetermined parameter, or for monitoring a predetermined condition, with extremely high precision.

According to one aspect of the present invention, there is provided a method of measuring the frequency of a cyclically-repeating electrical signal, comprising: passing the electrical signal through a network of sequentially-activated gates, in which the first gate detects the leading edge of each cycle of the electrical signal, and each of the remaining gates, when activated, applies a predetermined propagation delay to the detected leading edges; determining the gates which were activated at the beginning, and at the end, of a predetermined time window; determining the difference in the total propagation delays at the outputs of the activated gates; and utilizing the differences in the total propagation delays in determining the frequency of the electrical signal.

In the described preferred embodiments, the difference in the total propagation delays is utilized in determining the frequency of the electrical signal by counting the number of the leading edges detected during the predetermined time window, and dividing the number by the predetermined time window less the difference in the total propagation delays.

As will be described more particularly below, such a measuring method compensates for any change in phase of the electrical signal during the measuring period, and therefore enables much higher precision to be attained in the frequency measurement.

According to further features in the preferred embodiment of the invention described below, the predetermined time window is greater by at least one order of magnitude (three orders of magnitude in the described preferred embodiment) than the time period between adjacent detected edges of the electrical signal; each detected edge is also used to increment a counter; and the count in the counter is also used, together with the difference in the total propagation delay, in determining the frequency of the electrical signal. As will be described more particularly below, this feature, accumulates the frequency change over a long interval, and thereby also contributes to the high-precision attainable by the method of the present invention.

According to another aspect of the present invention, there is provided a method of measuring a predetermined parameter, or monitoring a predetermined condition, having a known relation to or influence on the transit time of movement of an energy wave through a medium, comprising:

(a) transmitting a cyclically-repeating wave of the energy through a transmission channel in the medium from a transmitter to a receiver at the opposite ends of the transmission channel;

(b) changing the frequency of the wave transmission such that the number of waves in a loop including the transmission channel is a whole integer; and (c) measuring the changes in frequency of the wave transmissions to provide a measurement of the predetermined parameter, or an indication of the predetermined condition, by;

(i) converting the cyclically-repeating energy wave transmitted through the transmission channel to a cyclically-repeating electrical signal;

(ii) passing the electrical signal through a network of sequentially-activated gates, in which the first gate detects the leading edge of each cycle of the electrical signal, and each of the remaining gates, when activated, applies a predetermined propagation delay to the detected leading edges;

(iii) determining the gates which were activated at the beginning, and at the end, of a predetermined time window;

(iv) determining the difference in the total propagation delays at the outputs of the activated gate; and (v) utilizing the difference in the total propagation delays in determining the frequency of the electrical signal.

According to further aspects of the present invention, there are provided apparatus for measuring the frequency of a cyclically-repeating electrical signal, and also apparatus for measuring a predetermined parameter or for monitoring a predetermined condition, according to the methods briefly described above, and to be described more particularly below.

Further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings.

THE PRIOR SYSTEM ILLUSTRATED IN FIG. 1

Figure 1:
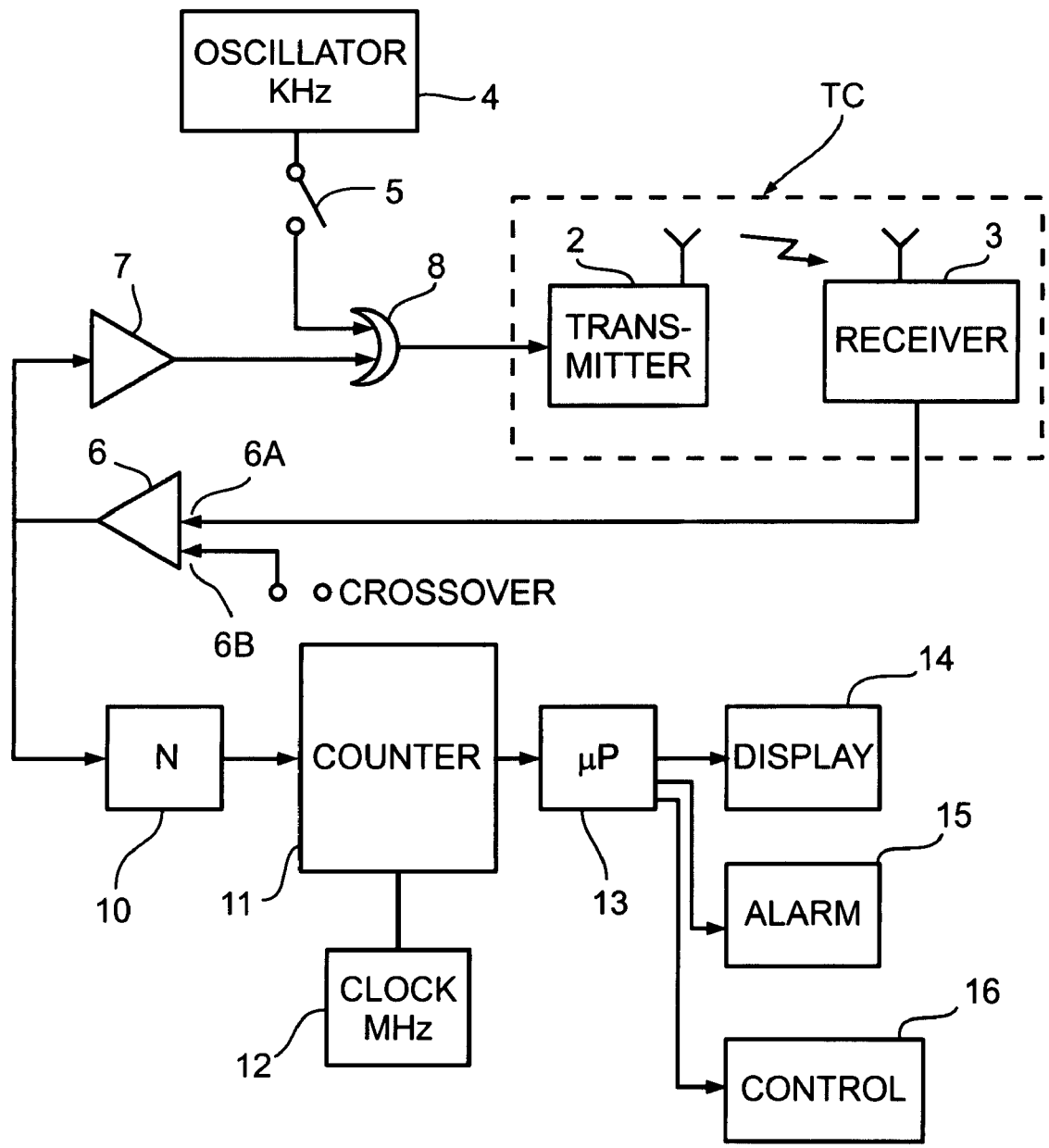
FIG. 1 is a block diagram illustrating a measuring system constructed in accordance with the above-cited U.S. Pat. No. 6,621,278 and U.S. Pat. No. 7,080,554 , based on the technique of detecting a predetermined fiducial point in each received wave transmitted through the transmission channel.

As indicated above, the prior system illustrated in FIG. 1 is described in the above-cited U.S. Pat. No. 6,621,278 and U.S. Pat. No. 7,080,554, the entire contents of which are expressly incorporated herein by reference. As further indicated above, the system illustrated in FIG. 1 is particularly useful for measuring a predetermined parameter, or monitoring a predetermined condition, having a known relation to or influence on the transit time of movement of an energy wave through a medium. For example, the energy wave may be an electromagnetic wave, an acoustical wave, a modulated carrier wave, an acoustical wave generated according to the "photoacoustical effect" by the impingement of an electromagnetic beam against a target, etc. The transmission channel may be a gas, a liquid or a solid; and the monitored condition may have a known relation to, or influence on, the transit velocity and/or the transit distance of the cyclically-repeating energy wave through the transmission channel.

In FIG. 1, the energy-wave transmission channel is indicated by the broken-line block TC. It includes a transmitter 2 for transmitting a cyclically-repeating wave of the energy through a transmission channel in the medium itself, and a receiver 3 at the opposite end of the transmission channel for receiving the transmitted wave.

Initially, the energy wave is continuously transmitted from an oscillator 4 under the control of a switch 5 until the waves are received by receiver 3. Once the waves are received, switch 5 is opened so that the received waves are thereafter used for controlling the frequency of transmission of the cyclically-repeating energy wave by transmitter 2.

As shown in FIG. 1, the signals received by receiver 3 are fed to a comparator 6 via its input 6a. Comparator 6 includes a second input 6b connected to a predetermined bias so as to detect a predetermined fiducial or reference point in the received signal. In the example illustrated in FIG. 1, this predetermined fiducial point is the "zero" cross-over point of the received signal, and therefore input 6b is at a zero-bias. Other reference points could be used as the fiducial point, such as the maximum or minimum peak of the received signals. As will be described below with respect to FIG. 2, the present invention uses yet another fiducial point, namely the leading edge of each cycle of the cyclically-repeating electrical signal outputted by the receiver 3.

The output of comparator 6 is fed to a monostable oscillator 7 which is triggered to produce an amplified output signal for each fiducial point in the signals received by the receiver 3. The signals from oscillator 7 are fed via an OR-gate 8 to transmitter 2. OR-gate 8 also initially receives the output from oscillator 4 when switch 5 is closed. However, when the transmitter 2 receives a continuous stream of signals from oscillator 7 via OR-gate 8, switch 5 is opened as indicated above. Accordingly, transmitter 2 will then transmit at a frequency determined by the fiducial points in the signals received by receiver 3 and detected by comparator 6. The frequency of transmission by transmitter 2 will therefore be such that the number of waves of the cyclically-repeating energy wave transmitted by transmitter 2 and received by receiver 3 is a whole integer.

It will thus be seen that while the frequency of the transmitter 2 will change with a change in the monitored condition's influence on the medium in the transmission channel TC, the number of wavelengths ($\lambda$) in the signal transmitted from the transmitter 2 to the receiver 3 will remain a whole integer. This is because the transmitter 2 transmissions are controlled by the fiducial points of the signals received by receiver 3. This change in frequency by the transmitter 2, while maintaining the number of waves in the loop of the transmission channel TC as a whole integer, enables a precise determination to be made of the transit distance or of the transit time through the transmission channel. Thus, as known:

$$F=C/\lambda$$

where: F and C are the frequency and velocity, respectively, of the cyclically-repeating energy wave in the respective medium; and $\lambda$ is the wavelength. For example, if the energy wave is an acoustical wave, and the medium is air under normal temperatures and pressures, C=340,000 mm/sec. Accordingly, if F=34 KHz, then $\lambda$–10 mm.

Assuming the initial transit distance is 100 mm, it will be seen that the number of wavelengths in this transit distance will be 10.

Now assume that the transit distance is increased by 1 mm, i.e., from 100 mm to 101 mm. When this transit distance is increased from 100 mm to 101 mm, the transit time will also be increased. However, since the frequency of transmitter 2 is controlled by the fiducial point of the signals received by receiver 3, the transmitter 2 will still produce the same number of waves during this increased transit time, and therefore the waves will be slightly increased in length. Thus, the increased wavelength will be 101/10=10.1 mm. The frequency of transmitter 2 will therefore be changed from 34 KHz to 340,000/10.1=33,663 KHz.

The frequency will thus be decreased by 337 Hz when the distance is increased by 1 mm. Such a frequency change can be easily measured. However, if the distance is changed by 0.001 mm (rather than 1 mm), the frequency change will be 0.337 Hz, which would be extremely difficult to measure according to conventional techniques. However, such a small frequency change can be easily measured in the system illustrated in FIG. 1 by including a summing circuit which continuously sums the measured frequency changes over a predetermined time, e.g., 100, 1,000, 10,000, or more cycles, and produces periodic readouts of the summed changes.

Thus, the waves outputted from comparator 6, which are used for controlling the frequency of the transmitter 2, are also fed to a counter 10 to be counted "N" times, and the output is fed to another counter 11 controlled by a clock 12. Counter 11 produces an output to a microprocessor 13 which performs the computations according to the parameter to be detected or measured. As shown in FIG. 1, microprocessor 13 controls a display 14 for displaying its output, an alarm 15 for alerting a user as to a possible alarm condition, and a control 16, e.g., a vibrator, which may be actuated when a particular condition is determined to be present.

Further details of the construction, use and possible applications of the circuit of FIG. 1 are set forth in the above-cited U.S. Pat. No. 6,621,278, and U.S. Pat. No. 7,080,554, the contents of which have been incorporated herein by reference. Other variations and applications of such a system are described in International Patent Applications PCT/IL02/00983 filed Dec. 5, 2002, and PCT/IL2004/000138 filed Feb. 12, 2004, the contents of which are also incorporated herein by reference.

It will be seen that in the system of FIG. 1, the fiducial point of each wave is determined by comparator 6. It will also be seen that comparator 6 also controls an amplifier (monostable oscillator 7), which may be used to compensate for the losses in the loop containing transmission channel TC.

THE IMPROVED SYSTEM OF THE PRESENT INVENTION

The present invention provides an improved method and apparatus for measuring the frequency of a cyclically-repeating electrical signal particularly useful in the method and apparatus described above with respect to FIG. 1. According to the present invention, the cyclically-repeating electrical signal whose frequency is to be measured is passed through a network of sequentially activated gates in which the first gate detects the leading edge of each cycle of the electrical signal, and each of the remaining gates, when activated, applies a predetermined propagation delay to the detected leading edges. Determinations are made of the gates which were activated at the beginning, and at the end, of a predetermined time window, and also of the difference in the total propagation delays at the outputs of such activated gate. The so determined difference in the total propagation delays is utilized in determining the frequency of the electrical signal.

In the example described below, the frequency of the cyclically-repeating electrical signal to be measured is in the order of one MHz, and therefore the time period between adjacent detected edges of the electrical signal would be in the order of a microsecond. In the described example, the network of gates includes in the order of 10,000 gates each having a propagation delay in the order of 100 picoseconds. Accordingly, such a measuring system would have a resolution of 100 picoseconds, which would correspond to a frequency error of about 0.1 Hz, rather than a frequency error of up to 1,000 cycles when the above-mentioned frequency measuring technique is used.

Another important advantage in the improved method and system of the present invention is that the system lends itself to digital implementation, thereby further increasing the resolution capability of the system, as well as facilitating its implementation in an ASIC (Application Specific Integrated Circuit) chip which can be produced in volume and at lost cost.

Figure 2:
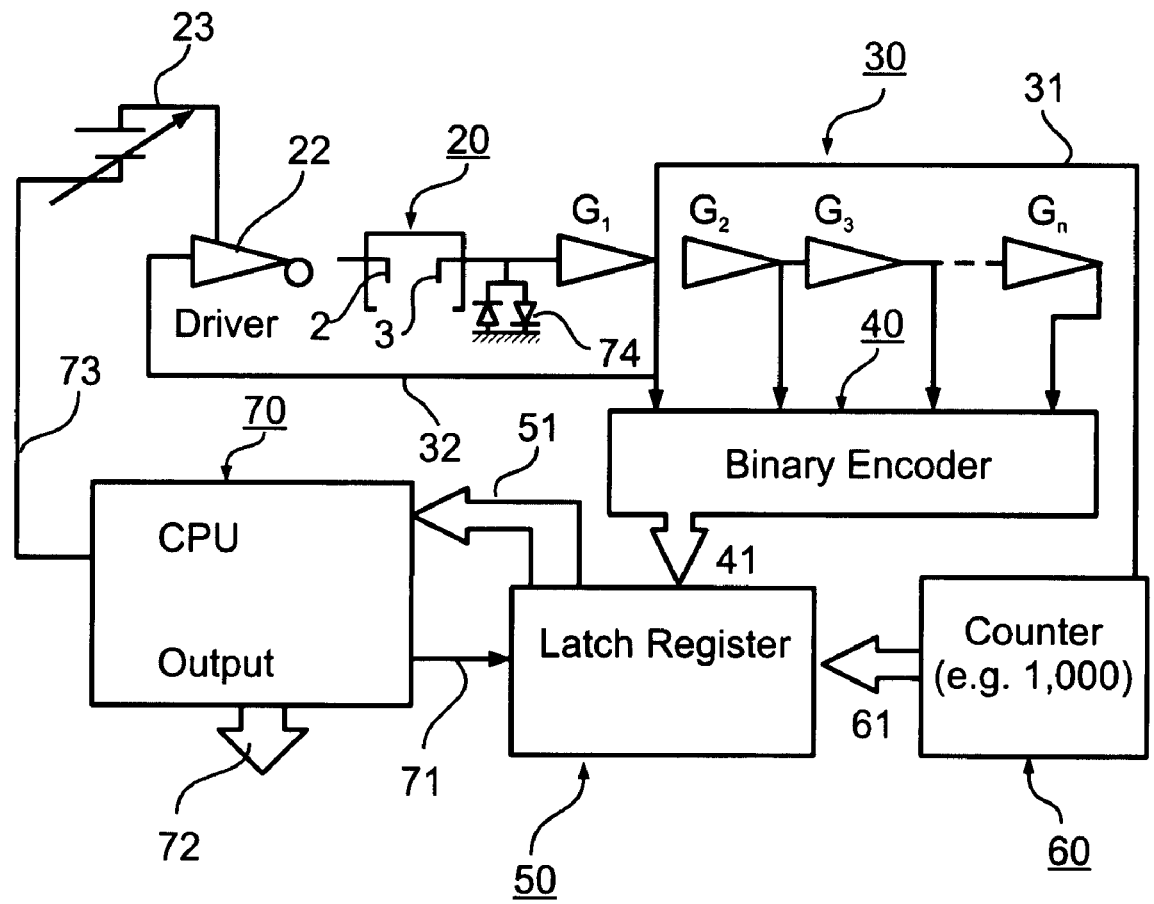
FIG. 2 is a block diagram illustrating an implementation of the system of FIG. 1 in accordance with the present invention to provide the advantages of the present invention as briefly mentioned above, and as to be described more particularly below.

FIG. 2 illustrates, for purposes of example, one implementation of the system of FIG. 1 in accordance with the present invention.

The system illustrated in FIG. 2 includes a transmission channel, generally designated 20, corresponding to transmission channel TC of FIG. 1, including an acoustical wave transmitter 2 and receiver 3 at the opposite ends of the channel. Transmitter 2 is driven by a driver 22. Driver 22 may a monostable oscillator or amplifier, corresponding to amplifier 7 in FIG. 1, which is capable of making up for transmission losses within the transmission channel 20. Preferably, however, driver 22 is controlled by a controllable voltage source 23 to make up the transmission losses, as will be described more particularly below.

Acoustical receiver 3, which detects the acoustical waves from transmitter 2, converts such acoustical waves to a cyclically-repeating electrical signal which is passed through a network, generally designated 30, of sequentially activated gates $G_1$-$G_n$. The first gate $G_1$ in network 30 detects the leading edge of each cycle of the electrical signal, and each of the remaining gates $G_2$-$G_n$, when activated, applies a predetermined propagation delay to the detected leading edges.

As one example, if the cyclically-repeating electrical signal inputted into network 30 is in the order of one MHz, gate network 30 may have 10,000 gates, each applying a propagation delay of 100 picoseconds. The total propagation delay for all the gates would therefore be one microsecond, thereby covering the time period between adjacent detected edges of the inputted electrical signal.

The system illustrated in FIG. 2 further includes a binary encoder 40 which encodes the status of the network 30 of sequentially activated gates $G_1$-$G_n$. The status of the gate network 30 is continuously outputted by binary coder 40, via its output 41, to a latch register 50.

The detected leading edge of each cycle of the electrical signal, as detected by the first gate $G_1$ of gate network 30, is applied via line 31 to increment a counter 60. Thus, counter 60 continuously counts the leading edge of each cycle of the electrical signal from receiver 3. As one example, counter 60 may count up to 1,000 leading edges before restarting the count.

As shown in FIG. 2, the output from the first gate $G_1$ of the gate network 30 is also applied via line 32 to trigger driver 22 of transmitter 2. Accordingly, in this embodiment, the fiducial point of the received electrical signal, for triggering the next signal from the transmitter, is the detected leading edge of the received signal rather than the "0" crossover point as in the FIG. 1 embodiment. Generally speaking, the leading edge of an electrical signal can be more precisely determined than the "0" crossover point, and therefore using the leading edge as the fiducial point further contributes to the high-precision of the system illustrated in FIG. 2.

The count within counter 60 is applied, via the counter output 61, as a second input to latch register 50. This input is in addition to the status of the gate network 30 as inputted into the latch register from the binary encoder 40 via its output line 41.

The system illustrated in FIG. 2 further includes a data processor 70 which, among other functions, defines a predetermined time window outputted via its line 71 to the latch register 50. Such a predetermined time window is preferably greater, by at least one order of magnitude, than the time period between adjacent detected edges of the electrical signal as detected by gate $G_1$ and counted by counter 60. In the example described, the time period between adjacent edges is in the order of one microsecond. In such case, the predetermined time window defined by processor 70, via its output line 71 to latch register 50, would be one millisecond so as to cover the 1,000 counts of counter 60.

Latch register 50 outputs to processor 70, via output line 51, the count in counter 60, and also the gate of network 30 which was last-activated at the beginning, and at the end, of the predetermined time window (one millisecond) defined by processor 70 via its output 71 to the latch register. This information, inputted into processor 70 via latch register output 51, is utilized by processor 70 to determine the total propagation delays at the outputs of the gates activated at the beginning, and at the end, of the predetermined time period. This information is also used by processor 70 to determine the frequency (Fx) of the electrical signal from receiver 3 of the transmission channel 20, as follows:

$$Fx = \frac{N}{\Delta T - (ts_2 - ts_1)}$$

wherein: N is the number of leading edges detected by counter 60 during the predetermined time window ($\Delta T$);

$ts_1$ is the total propagation delay at the output of the last-activated gate, with respect to the first gate, at the start of said predetermined time window; and $ts_2$ is the total propagation delay at the output of the last-activated gate, with respect to the first gate, at the end of said predetermined time window.

Figure 3:
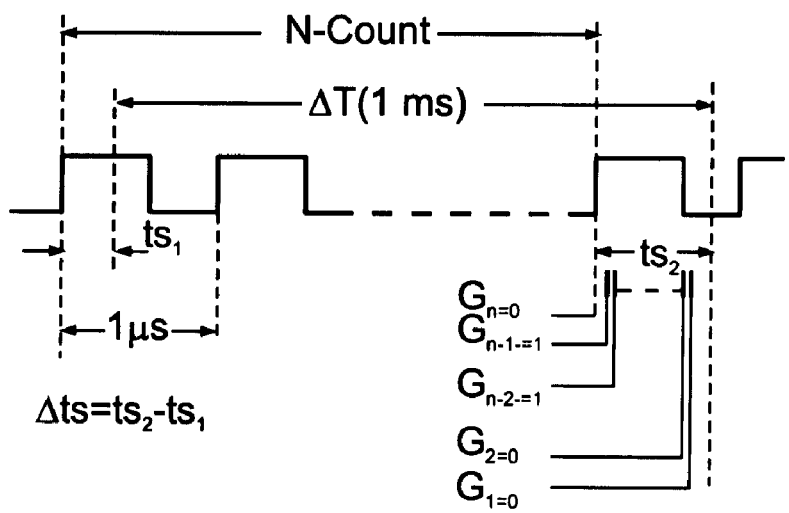
FIG. 3 is a diagram helpful in explaining the present invention.

The foregoing is illustrated in the diagram of FIG. 3. The frequency measurement determined by processor 70 is outputted via its output line 72, for control, display or alarm purposes.

In the example described above, the frequency of the electrical signal from receiver 3 is in the order of one MHz, such that the time period between detected leading edges is one microsecond; counter 60 has a capacity of 1,000 counts; network 30 includes 10,000 gates each imposing a propagation delay of 100 picoseconds; and processor 70 defines, in its line 71 to latch register 50, a predetermined time window of one millisecond. The error in the frequency measurement would therefore be up to 100 picoseconds, corresponding to a frequency error of 0.1 microHz.

It will be appreciated such a low frequency error enables an extremely high resolution to be attained in the frequency measurement. This in turn enables the predetermined parameter (e.g., distance, displacement, temperature, pressure, force, etc.) to be measured by the overall system with extremely high precision. It will also be appreciated that the resolution can be further increased or decreased, according to the particular application, by appropriately designing the gate network 30 to provide the propagation delay at each gate according to the resolution required. It will be further appreciated that the determination of the frequency can be done by digital circuitry, thereby facilitating its implementation by means of an ASIC (Application Specific Integrated Circuit) chip, permitting high volume lost cost production.

As indicated earlier, processor 70 may also control, via its line 73, the variable voltage source 23 connected to driver 22 to compensate for losses within the transmission loop. The system illustrated in FIG. 2 further includes an over-voltage protection circuit, in the form of back-to-back diodes 74, between the receiver 3 of transmission channel 20 and the first gate $G_1$, of gate network 30.

Although the invention has been described in conjunction with specific embodiments thereof, it is evident that many alternatives, modifications and variations will be apparent to those skilled in the art. For example, the method of measuring frequency described herein may be used with a measuring system based on the phase locked loop embodiment illustrated in U.S. Pat. No. 7,080,554, or in many other systems requiring a precise measurement of frequency. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of measuring the frequency of a cyclically-repeating electrical signal, comprising:

passing said electrical signal through a network of sequentially-activated gates, in which the first gate detects the leading edge of each cycle of said electrical signal, and each of the remaining gates, when activated, applies a predetermined propagation delay to said detected leading edges;

determining the gates which were activated at the beginning, and at the end, of a predetermined time window;

determining the difference in the total propagation delays at the outputs of said activated gates; and utilizing said differences in the total propagation delays in determining the frequency of said electrical signal.

2. The method according to claim 1, wherein said difference in the total propagation delays is utilized in determining the frequency of said electrical signal by counting the number of said leading edges detected during said predetermined time window, and dividing said number by said predetermined time window less said difference in the total propagation delays.

3. The method according to claim 1, wherein said network includes a sufficient number of gates such that the total propagation delay for all the gates in said network covers the time period between adjacent detected edges of said electrical signal.

4. The method according to claim 3, wherein the time period between adjacent detected edges of said electrical signal is in the order of a microsecond, and wherein said network includes in the order of 10,000 gates each having a propagation delay in the order of 100 picoseconds.

5. The method according to claim 1, wherein:

said predetermined time window is greater by at least one order of magnitude than the time period between adjacent detected edges of said electrical signal;

each detected edge is also used to increment a counter; and the count in said counter is also used, together with said difference in the total propagation delays, in determining the frequency of said electrical signal.

6. The method according to claim 5, wherein:

the time period between adjacent detected edges of the electrical signal is in the order of a microsecond;

said predetermined time window is in the order of a millisecond; and said predetermined propagation delay at each gate is in the order of 100 picoseconds.

7. The method according to claim 5, wherein said frequency (Fx) is determined as follows:

$$Fx = \frac{N}{\Delta T - (ts_2 - ts_1)}$$

wherein: N is the number of said leading edges detected during said predetermined time window ($\Delta T$);

$ts_1$ is the total propagation delay at the output of the last-activated gate, with respect to the first gate, at the start of said predetermined time window; and $ts_2$ is the total propagation delay at the output of the last-activated gate, with respect to the first gate, at the end of said predetermined time window.

8. A method of measuring a predetermined parameter, or monitoring a predetermined condition, having a known relation to or influence on the transit time of movement of an energy wave through a medium, comprising:

(a) transmitting a cyclically-repeating wave of said energy through a transmission channel in said medium from a transmitter to a receiver at the opposite ends of said transmission channel;

(b) changing the frequency of said wave transmission such that the number of waves in a loop including said transmission channel is a whole integer; and (c) measuring the changes in frequency of the wave transmissions to provide a measurement of said predetermined parameter, or an indication of said predetermined condition, by;

(i) converting said cyclically-repeating energy wave transmitted through said transmission channel to a cyclically-repeating electrical signal;

(ii) passing said electrical signal through a network of sequentially-activated gates, in which the first gate detects the leading edge of each cycle of said electrical signal, and each of the remaining gates, when activated, applies a predetermined propagation delay to said detected leading edges;

(iii) determining the gates which were activated at the beginning, and at the end, of a predetermined time window;

(iv) determining the difference in the total propagation delays at the outputs of said activated gates; and (v) utilizing said difference in the total propagation delays in determining the frequency of said electrical signal.

9. The method according to claim 8, wherein said difference in the total propagation delays is utilized in determining the frequency of said electrical signal by counting the number of said leading edges detected during said predetermined time window, and dividing said number by said predetermined time window less said difference in the total propagation delay.

10. The method according to claim 8, wherein said network includes a sufficient number of gates such that the total propagation delay for all the gates in said network covers the time period between adjacent detected edges of said electrical signal.

11. The method according to claim 10, wherein the time period between adjacent detected edges of said electrical signal is in the order of a microsecond, and wherein said network includes in the order of 10,000 gates each having a propagation delay in the order of 100 picoseconds.

12. The method according to claim 8, wherein:

said predetermined time window is greater by at least one order of magnitude than the time period between adjacent detected edges of said electrical signal;

each detected edge is also used to increment a counter; and the count in said counter is also used, together with said difference in the total propagation delay, in determining the frequency of said electrical signal.

13. The method according to claim 12, wherein:

the time period between adjacent detected edges of the electrical signal is in the order of a microsecond;

said predetermined time period window is in the order of a millisecond; and said predetermined propagation delay at each gate is in the order of 100 picoseconds.

14. The method according to claim 12, wherein said frequency (Fx) is determined as follows:

$$Fx = \frac{N}{\Delta T - (ts_2 - ts_1)}$$

wherein: N is the number of said leading edges detected during said predetermined time window ($\Delta T$);

ts₁ is the total propagation delay at the output of the last-activated gate, with respect to the first gate, at the start of said predetermined time window; and ts₂ is the total propagation delay at the output of the last-activated gate, with respect to the first gate, at the end of said predetermined time window.

15. The method according to claim 8, wherein a controllable voltage source is provided and is controlled to compensate for losses in the loop of said transmission channel.

16. The method according to claim 15, wherein said controllable voltage source is connected to a driver for said transmitter and is controlled by a processor to compensate for losses in the loop of said transmission channel.

17. The method according to claim 16, wherein said processor also determines the last gate in said network which was last-activated upon the expiration of said predetermined time window.

18. The method according to claim 16, wherein an overvoltage protection circuit is provided between said receiver and said network of gates.

19. The method according to claim 8, wherein the frequency of said wave transmission is changed in accordance with a detected fiducial point of each received wave such that the number of waves in the loop including said transmission channel is a whole integer.

20. The method according to claim 19, wherein said detected fiducial point is the leading edge of each received wave and is detected by the first gate of said network of gates.

21. Apparatus for measuring the frequency of a cyclically-repeating electrical signal, comprising:
a network of sequentially-activated gates for receiving said cyclically-repeating electrical signal, the first gate in said network detecting the leading edge of each cycle of said electrical signal, each of the remaining gates of said network, when activated, applying a predetermined propagation delay to said detected leading edges; and
a data processor for:
determining the gates which were activated at the beginning, and at the end, of a predetermined time window;
determining the difference in the total propagation delays at the outputs of said activated gates; and
utilizing said difference in the total propagation delays in determining the frequency of said electrical signal.

22. The apparatus according to claim 21, wherein said difference in the total propagation delays is utilized in determining the frequency of said electrical signal by counting the number of said leading edges detected during said predetermined time window, and dividing said number by said predetermined time window less said difference in the total propagation delays.

23. The apparatus according to claim 21, wherein said network includes a sufficient number of gates such that the total propagation delay for all the gates in said network covers the time period between adjacent detected edges of said electrical signal.

24. The apparatus according to claim 23, wherein the time period between adjacent detected edges of said electrical signal is in the order of a microsecond, and wherein said network includes in the order of 10,000 gates each having a propagation delay in the order of 100 picoseconds.

25. The apparatus according to claim 23, wherein said predetermined time window is greater by at least one order of magnitude than the period between adjacent detected edges; and wherein said data processor is in a data processing system which also includes a counter incremented by each detected edge, and which utilizes the count in said counter, together with said difference in the total propagation delays, in determining the frequency of the electrical signal.

26. The apparatus according to claim 25, wherein:
the time period between adjacent detected edges of the electrical signal is in the order of a microsecond;
said predetermined time window is in the order of a millisecond; and
said predetermined propagation delay at each gate is in the order of 100 picoseconds.

27. The apparatus according to claim 25, wherein said dataprocessor system determined the frequency (Fx) as follows:

$$Fx = \frac{N}{\Delta T - (ts_2 - ts_1)}$$

wherein: N is the number of said leading edges detected during said predetermined time window ($\Delta T$);
ts₁ is the total propagation delay at the output of the last-activated gate, with respect to the first gate, at the start of said predetermined time window; and
ts₂ is the total propagation delay at the output of the last-activated gate, with respect to the first gate, at the end of said predetermined time window.

28. The apparatus according to claim 25, wherein said data processor system further comprises:
a binary encoder for encoding the status of said network of sequentially-activated gates; and
a latch register having an input from said binary encoder, and another input from said counter;
said data processor being controlled by said latch register and producing an output representing the measured frequency.

29. Apparatus for measuring a predetermined parameter, or monitoring a predetermined condition, having a known relation to or influence on the transit time of movement of an energy wave through a medium, comprising:
a transmitter for transmitting a cyclically-repeating wave of said energy through a transmission channel in said medium from one end thereof;
a receiver at the opposite end of said transmission channel for receiving said transmitted wave and for converting same to a cyclically-repeating electrical signal; and
a data processing system for changing the frequency of said wave transmission such that the number of waves in a loop including said transmission channel is a whole integer, and for measuring the changes in frequency of the wave transmissions to provide a measurement of said predetermined parameter or an indication of said predetermined condition:
said data processing system including a network of sequentially-activated gates for receiving said cyclically-repeating electrical signal, the first gate in said network detecting the leading edge of each cycle of said electrical signal, each of the remaining gates of said network, when activated, applying a predetermined propagation delay to said detected leading edges;
said data processing system further including a data processor for:

determining the gates which were activated at the beginning, and at the end, of a predetermined time window;

determining the difference in the total propagation delays at the outputs of said activated gates; and utilizing said difference in the total propagation delays in determining the frequency of said electrical signal.

30. The apparatus according to claim 29, wherein said difference in the total propagation delays is utilized in determining the frequency of said electrical signal by counting the number of said leading edges detected during said predetermined time period, and dividing said number by said predetermined time window less said difference in the total propagation delay.

31. The apparatus according to claim 29, wherein said network includes a sufficient number of gates such that the total propagation delay for all the gates in said network covers the time period between adjacent detected edges of said electrical signal.

32. The apparatus according to claim 31, wherein the time period between adjacent detected edges of said electrical signal is in the order of a microsecond, and wherein said network includes in the order of 10,000 gates each having a propagation delay in the order of 100 picoseconds.

33. The apparatus according to claim 31, wherein said predetermined time window is greater by at least one order of magnitude than the time period between adjacent detected edges; and wherein said data processing system also includes a counter incremented by each detected edge and utilizes the count in said counter, together with said difference in the total propagation delays, in determining the frequency of the electrical signal.

34. The apparatus according to claim 33, wherein:

said time period between adjacent detected edges of the electrical signal is in the order of a microsecond;

said predetermined time window is in the order of a millisecond; and said predetermined propagation delay at each gate is in the order of 100 picoseconds.

35. The apparatus according to claim 33, wherein said dataprocessor system $$Fx = \frac{N}{\Delta T - (ts_2 - ts_1)}$$

determined the frequency (Fx) as follows:

wherein: N is the number of said leading edges detected during said predetermined time window ($\Delta T$);

$ts_1$ is the total propagation delay at the output of the last-activated gate, with respect to the first gate, at the start of said predetermined time window; and $ts_2$ is the total propagation delay at the output of the last-activated gate, with respect to the first gate, at the end of said predetermined time window.

36. The apparatus according to claim 33, wherein said data processor system further comprises:

a binary encoder for encoding the status of said network of sequentially-activated gates; and a latch register having an input from said binary encoder, and another input from said counter;

said data processor being controlled by said latch register and producing an output representing the measured frequency.

37. The apparatus according to claim 29, wherein said apparatus further comprises a controllable voltage source which is controlled to compensate for losses in the loop of said transmission channel.

38. The apparatus according to claim 36, wherein said controllable voltage source is connected to a driver for said transmitter and is controlled by said data processor to compensate for losses in the loop of said transmission channel.

39. The apparatus according to claim 37, wherein said apparatus further comprises an over-voltage protection circuit between said receiver and said network of gates.

40. The apparatus according to claim 29, wherein said processor changes the frequency of said wave transmission in accordance with a detected fiducial point of each received wave such that the number of waves in the loop including said transmission channel is a whole integer.

41. The apparatus according to claim 40, wherein said detected fiducial point is the leading edge of each received wave and is detected by the first gate in said network of gates.

* * * * *